(12) United States Patent
Shekalim (10) Patent No.: US 6,974,438 B2
(45) Date of Patent: Dec. 13, 2005

(54) METHOD AND DEVICE FOR DETECTING MALFUNCTION IN A GRAVITY FED INTRAVENOUS DELIVERY SYSTEM

(75) Inventor: Avraham Shekalim, Nesher (IL)

(73) Assignee: L.G. Med Ltd., Nesher (IL)

( * ) Notice: Subject to any disclaimer, the term of this patent is extended or adjusted under 35 U.S.C. 154(b) by 371 days.

(21) Appl. No.: 09/982,853

(22) Filed: Oct. 22, 2001

(65) Prior Publication Data

US 2003/0078547 A1 Apr. 24, 2003

(51) Int. Cl.$^7$ .......................... A61M 31/00; A61M 1/00
(52) U.S. Cl. .......................................... 604/65; 604/118
(58) Field of Search .............................. 604/65, 31, 34, 604/118, 250, 67, 80, 81, 133, 153, 253, 255, 260; 128/DIG. 13

(56) References Cited

U.S. PATENT DOCUMENTS

| | | | |
|---|---|---|---|
| 3,901,231 A | * | 8/1975 | Olson .......................... 604/152 |
| 4,010,749 A | | 3/1977 | Shaw |
| 4,378,808 A | | 4/1983 | Lichenstein |
| 4,534,756 A | | 8/1985 | Nelson |
| 4,784,648 A | * | 11/1988 | Singh et al. ................. 604/141 |
| 4,816,019 A | | 3/1989 | Kamen |
| 4,877,034 A | * | 10/1989 | Atkins et al. ................ 600/475 |
| 5,647,853 A | | 7/1997 | Feldmann et al. |
| 5,964,703 A | | 10/1999 | Goodman et al. |

\* cited by examiner

*Primary Examiner*—Brian L. Casler
*Assistant Examiner*—Lina R Kontos
(74) *Attorney, Agent, or Firm*—Mark M. Friedman (57) ABSTRACT

Described is an accurate, easy to use and inexpensive device and method for substantially immediate detection and indication of malfunction in an intravenous delivery system. The two piece device includes a disposable conduit body interconnected with the tubing of an intravenous delivery system and a reusable clamp apparatus that is deployed around the conduit body. The conduit body is highly sensitive to pressure changes inside the tubing. The clamp apparatus contains a sensing mechanism that discerns the responses of the conduit body to the change in line pressure from below to above atmospheric pressure. Also located in the clamp apparatus is an indication system that indicates if that change in pressure has occurred.

21 Claims, 7 Drawing Sheets

METHOD AND DEVICE FOR DETECTING MALFUNCTION IN A GRAVITY FED INTRAVENOUS DELIVERY SYSTEM

FIELD AND BACKGROUND OF THE INVENTION

The present invention relates to detection of malfunction during intravenous delivery of fluids and, in particular, it concerns a method and device for detecting malfunction in gravity fed intravenous delivery systems.

It is known a common malfunction encountered in intravenous fluid administration is the infiltration of the fluids into tissues near the tip of the catheter. This phenomenon, variously referred to as "infiltration" and "extravasation", may occur in a number of different ways. Often it is due to the tip of the catheter penetrating the wall of the vine or artery into which the catheter has been inserted, the tip thereby becoming lodged in the surrounding tissue. Although some texts distinguish between the terms infiltration and extravasation, they are widely used, and will be herein, interchangeably to denote generically any and all circumstances in which intravenous fluid delivery spreads beyond the blood vessel to adjacent tissue. Extravasation may lead to discoloration, discomfort and tissue destruction as well as lack of delivery of the intravenous fluids or drugs into the patient's system. Infiltration of certain drugs into the patient's tissues may be dangerous or cause serious damage, such as necrosis, requiring amputation or other surgical procedures.

Several methods, and device for their implementation, have been proposed for the detection of tissue infiltration during intravenous administration of fluids. One approach is by monitoring the flow rate or pressure of fluid in the tubing supplying the fluid to the catheter. Examples of devices based on such methods are disclosed in U.S. Pat. No. 4,534,756 to Nelson, U.S. Pat. No. 4,784,648 to Singh et al., and U.S. Pat. No. 5,647,853 to Feldmann et al. Commercially available device based on these techniques, however, are generally ineffective since the pressure differences indicative of extravasation are typically small in relation to other causes of pressure variations in an intravenous delivery system during use, such as patient movements or changes in the head pressure of an infusion bag.

A second method for the detection of extravasation is based upon changes in skin temperature in areas where extravasation has occurred. This is due to the temperature deferential between the intravenous fluids and the tissues in which they have accumulated. Examples of these types of devices are described in U.S. Pat. No. 4,010,749 to Shaw and U.S. Pat. No. 4,378,808 to Lichtenstein, which do not work well when the temperature deferential is not significant and false alarms may result from changes in the ambient temperature. Further, devices based on this method, even those that are able to overcome the above-mentioned problems, are intended for the detection of extravasation and are ineffective for detection of other malfunctions.

Additional examples of proposed techniques include measurements of conductivity (e.g. U.S. Pat. No. 5,964,703 to Goodman et al.) and measurements of spectral reflection (e.g. U.S. Pat. No. 4,877,034 to Atkins et al.).

The devices in all of the categories mentioned above suffer from high cost, reliability limitations or complexity of operation. Many of them require calibration before use and the calibrations may be set to accept an inappropriate initial positioning of a catheter thereby allowing extravasation to occur undetected. Thus, the predominant technique for identifying extravasation remains visual inspection by medical personnel of the area surrounding the catheter for swelling or other signs of infiltration. To be effective, this technique requires continual monitoring by trained medical personnel.

It is further known that a number of malfunctions, in addition to extravasation, result in the slowing or total stoppage of the fluid flow in the intravenous delivery system. Methods and devices for monitoring fluid flow include those that monitor flow-rate or pressure such as the devices mentioned above and the device of U.S. Pat. No. 4,816,019 to Kamen, which monitors pressure changes in a negative pressure stepping means. The data generated is processed at compared to data from previous intervals and a predetermine criteria for malfunction. This method, therefore, does not provide an immediate indication of malfunction.

Another method includes devices that count the drops that fall from the fluid bag into the accumulator at the top of the delivery tubing. Variations in that drop-rate are used to determine corresponding variations in the flow-rate of the fluid through the tubing. These devices are susceptible to false indications due to conditions other than malfunction such as change in head pressure in the fluid bag or change of patient position.

There is therefore a need for an accurate, easy to use and inexpensive device and method for continuous monitoring and substantially immediate detection and indication of a malfunction that causes a stoppage or significant slowing in the flow rate in an intravenous delivery system. Especially when the malfunction may be an indication of extravasation of fluid into tissue surrounding the tip of the catheter. It would also be highly advantageous for a device to include components that do not require calibration and would be able to indicate initial malfunction or inappropriate initial placement of the catheter. It would be desirable for components of the device that come in direct contact with the fluid to be disposable components.

SUMMARY OF THE INVENTION

The present invention is a method and device for detecting malfunction in a gravity fed intravenous delivery system.

According to the teachings of the present invention there is provided, a device for detecting malfunction of a gravity fed intravenous delivery system that includes a fluid reservoir, a fluid flow-rate valve, and tubing for delivery of the fluid from the container to a catheter, the catheter being inserted intravenously in a patient, the device comprising: a) a conduit body including: a housing configured for interconnection with the tubing, fluid flowing through an interior flow passage in the housing, the housing including at least one pressure release passage to allow the fluid to pass between the interior passage and a pressure-sensing region; and an elastic non-permeable sheath deployed so as to circumscribe the housing such that the pressure-sensing region is located between an exterior wall of the housing and the sheath; b) a sensing mechanism deployed around the conduit body, the sensing mechanism including at least one sensor configured to discern the expansion of the sheath, the expansion being caused by an increase of the fluid in the pressure sensing region due to increased fluid pressure in the tubing and the housing; and c) an indication system coupled to the sensor.

According to a further teaching of the present invention, the housing has a shape such that the length of an outer periphery of a cross-section is substantially constant for any cross-section along the length of the housing.

According to a further teaching of the present invention, a cross-section of the housing taken at a point in either end region will have a substantially circular outer shape to facilitate interconnection with the tubing, and a cross-section taken at a point in a middle region will have a substantially elongated outer shape configured to provide a substantially flat area for the pressure-sensing region.

According to a further teaching of the present invention, the housing further includes a pattern of flow channels located in the pressure-sensing region substantially encircling an open end of the pressure-release passage, the flow channels being configured so as to facilitate diffusion of the fluid within the pressure-sensing region.

According to a further teaching of the present invention, the flow channels are formed between ridges that extend above a surface of the exterior wall.

According to a further teaching of the present invention, the sensor includes electrical contacts deployed around the conduit body.

According to a further teaching of the present invention, the discernment includes a change in status of the electrical contacts.

According to a further teaching of the present invention, the change in status includes the separation of the electrical contacts thereby opening an electrical circuit, the separation being caused by the expansion of the sheath.

According to a further teaching of the present invention, the sensing mechanism and indication system are housed in a clamp apparatus configured for repeated deployment, the deployment being around the conduit body.

According to a further teaching of the present invention, an audible indication is emitted by the indication system.

According to a further teaching of the present invention, a visual indication is emitted by the indication system.

According to a further teaching of the present invention, the sensing mechanism is battery powered.

According to a further teaching of the present invention, the indication system is battery powered.

There is provided according to a further feature of the present invention, a method for detecting malfunction of a gravity fed intravenous delivery system that includes a fluid reservoir, a fluid flow-rate valve, and tubing for delivery of the fluid from the container to the catheter, the catheter being inserted intravenously in a patient, the method comprising: a) monitoring pressure inside the tubing substantially proximal to and after the flow-rate valve along a flow path of the intravenous delivery system; and b) activating an alarm when the pressure inside the tubing exceeds atmospheric pressure.

According to a further teaching of the present invention, the monitoring is accomplished by: a) interconnecting a conduit body with the tubing, the conduit body including: a housing configured for interconnection with the tubing, fluid flowing through an interior flow passage in the housing, the housing including at least one pressure release passage to allow the fluid to pass between the interior passage and a pressure-sensing region; and an elastic non-permeable sheath deployed so as to circumscribe the housing such that the pressure-sensing region is located between an exterior wall of the housing and the sheath; b) deploying a sensing mechanism around the conduit body, the sensing mechanism including at least one sensor configured to discern the expansion of the sheath, the expansion being caused by an increase of the fluid in the pressure sensing region due to increased fluid pressure in the tubing and the housing, the sensing mechanism being further connected to an indication system.

According to a further teaching of the present invention, the discerning includes a change in the status of electrical contacts that are deployed around the conduit body, the electrical contacts being included in the sensing mechanism.

According to a further teaching of the present invention, the change in the status includes separating the electrical contacts thereby opening an electrical circuit, the separation being caused by the expansion of the sheath.

According to a further teaching of the present invention, the separation of the electrical contacts activates the indication system.

According to a further teaching of the present invention, the activation of the alarm causes the emittance of an audible indication.

According to a further teaching of the present invention, the activation of the alarm causes the emittance of a visual indication.

There is provided according to a further feature of the present invention, a system for the intravenous delivery of a fluid into a patient, the system comprising: the device of claim 1; tubing interconnected with a fluid flow-rate valve and the conduit body, so as to be a single unit; a fluid reservoir, configured for interconnection with a top termination of the tubing such that the path of fluid flow passes from the reservoir, through the flow-rate valve, the conduit body, and a remainder of the tubing; a catheter configured for interconnection with a bottom termination of the tubing; and a clamp apparatus housing the sensing mechanism and the indication system, the clamp apparatus configured for deployment around the conduit body.

BRIEF DESCRIPTION OF THE DRAWINGS

The invention is herein described, by way of example only, with reference to the accompanying drawings, wherein:

FIG. 6 and FIG. 7 are isometric views of an intravenous delivery system including the components of a preferred embodiment of the present invention. FIG. 6 shows the clamp apparatus ready for deployment around the conduit body, and FIG. 7 shows the clamp deployed.

DESCRIPTION OF THE PREFERRED EMBODIMENTS

The present invention is a method and device for detecting malfunction in a gravity fed intravenous delivery system.

The principles and operation of methods and devices according to the present invention may be better understood with reference to the drawings and the accompanying description.

By way of introduction, it will be useful to describe the underlying principles of the present invention. The present invention uses principles relating to pressures in columns of fluid, specifically columns inside conduits or tubes. A column of fluid in a tube that is closed at the bottom and open at the top will have pressures that are equal to atmospheric pressure at the top of the column and increase toward the bottom in proportion to the increased weight of the fluid above. A column in a tube with an open bottom and a closed top will be held in place in the tube by the atmospheric pressure exerted on the bottom of the column. The highest pressure is the atmospheric pressure at the bottom of the column and the pressure will decrease toward the top in proportion to the decreased weight of the fluid above. When an intravenous delivery system is functioning normally, the flow impedance is greater at the flow-rate valve than at the catheter. That is, the catheter is able to let more fluid out of the tubing than the flow-rate valve is letting in. In such a case, the pressure distribution within the column of fluid in the tubing will exhibit an abrupt drop to below atmospheric pressure analogous to the column in a tube with an open bottom and closed top, mentioned above. The pressure will be highest at the tip of the catheter, decrease toward the top, and be lowest directly under the flow-rate valve. That is, somewhere along the length of the tubing between the flow-rate valve and the catheter. When the intravenous delivery system is functioning properly, the pressure inside the tubing directly below the flow-rate valve is below atmospheric pressure, herein referred to as negative pressure. By the time the fluid reaches the catheter, the pressure inside the tubing is above atmospheric pressure, herein referred to as positive pressure. It is this phenomenon of change from negative pressure to positive pressure that the present invention uses to detect a malfunction during the intravenous delivery of fluid. When in-flow is greater than out-flow there is positive pressure along the entire length of the tubing, as in the case of the tube with the open top and closed bottom. Extravasation is a common problem that is the result of the catheter tip being located in body tissue rather than in the intended blood vessel. When the catheter tip is located in tissue, the fluid is not able to flow as freely as if it were positioned properly in the blood vessel and for the purposes of the present invention, the intravenous delivery system functions as if the catheter were closed. This results in positive pressure along the entire length of the tubing, thereby activating the indicator system of the present invention. This is true for any restriction of flow that occurs below the flow-rate valve and impedance is greater the than flow rate at the flow-rate valve. Restriction may be caused by kinked or pinched tube, or by a catheter tip that has become clogged by blood or other material.

Figure 1:
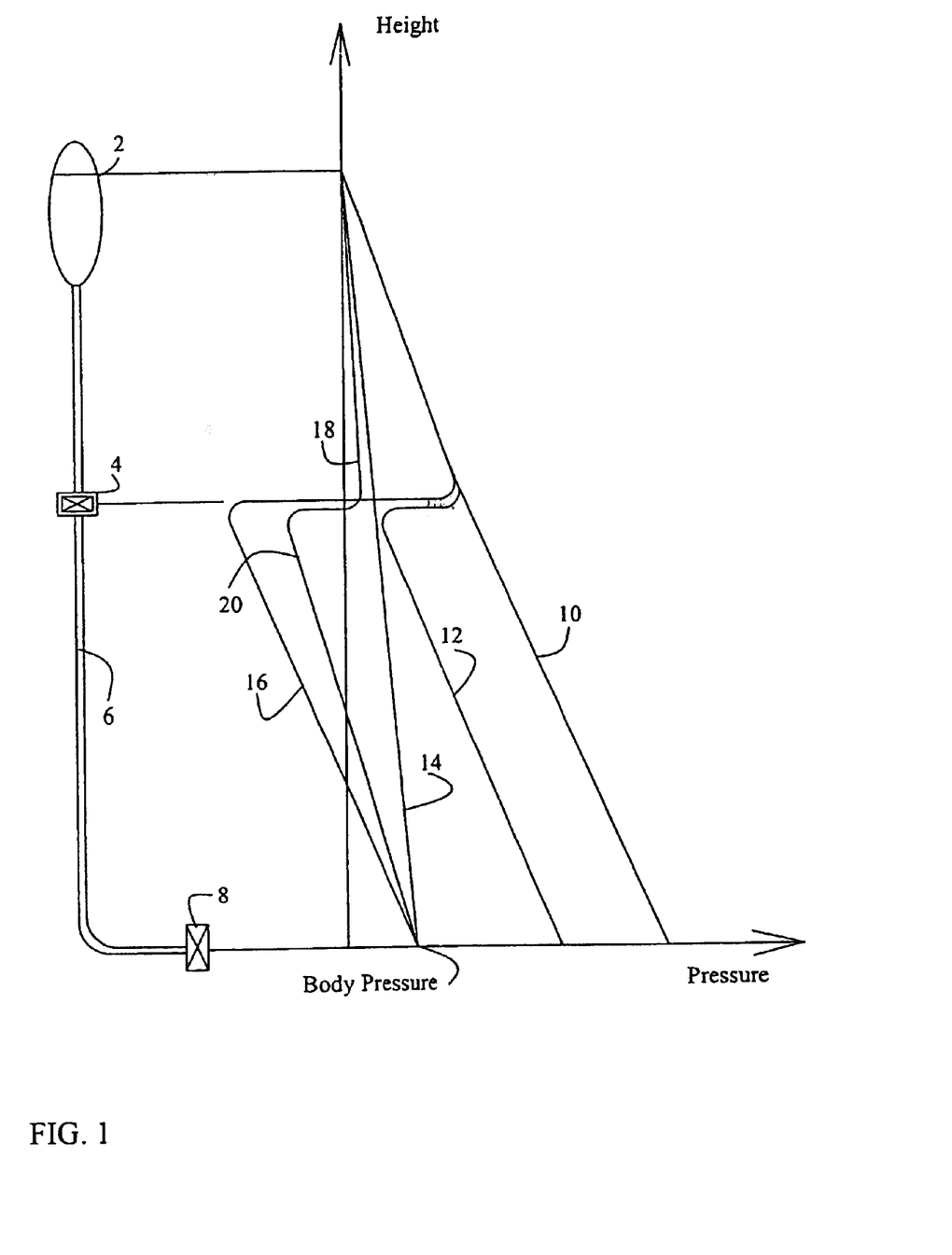
FIG. 1 is a schematic of an intravenous delivery system aligned with a graph of the various pressures within the system.

Referring now to the drawings, FIG. 1 shows a schematic view of an intravenous delivery system comprised of a fluid reservoir 2, a flow-rate valve 4, delivery tubing 6, and a catheter 8. To the right of, and correspondingly aligned with, the schematic is a graphic representation of the pressure inside the tubing along the entire system. Line 10 is the result of an open valve and a closed catheter, which has pressure caused by the column of fluid from the reservoir to the catheter. Line 12 is the result of a closed flow-rate valve and a closed catheter, which creates two columns of fluid, a first column above the valve and a second column between the valve and the catheter. Lines 14, 16, and 18 show the respective pressure when the catheter is properly inserted into, and functioning properly within the desired blood vessel. In all three cases, the maximum pressure is equal to body pressure, and the corresponding pressure through out the system is dependent on the amount of resistance caused by the valve. Line 14, which has one column of fluid, is the result of the valve being completely open with no fluid regulation. Both lines 16 and 18, which have two columns of fluid, result from the valve regulating the flow of the fluid at least partially. Line 18 is representative of the pressures in the system during normal proper functioning usage. As such, the present invention is most concerned with the phenomenon of the drop to negative pressure 20 that occurs directly below the flow-rate valve.

Figure 2:
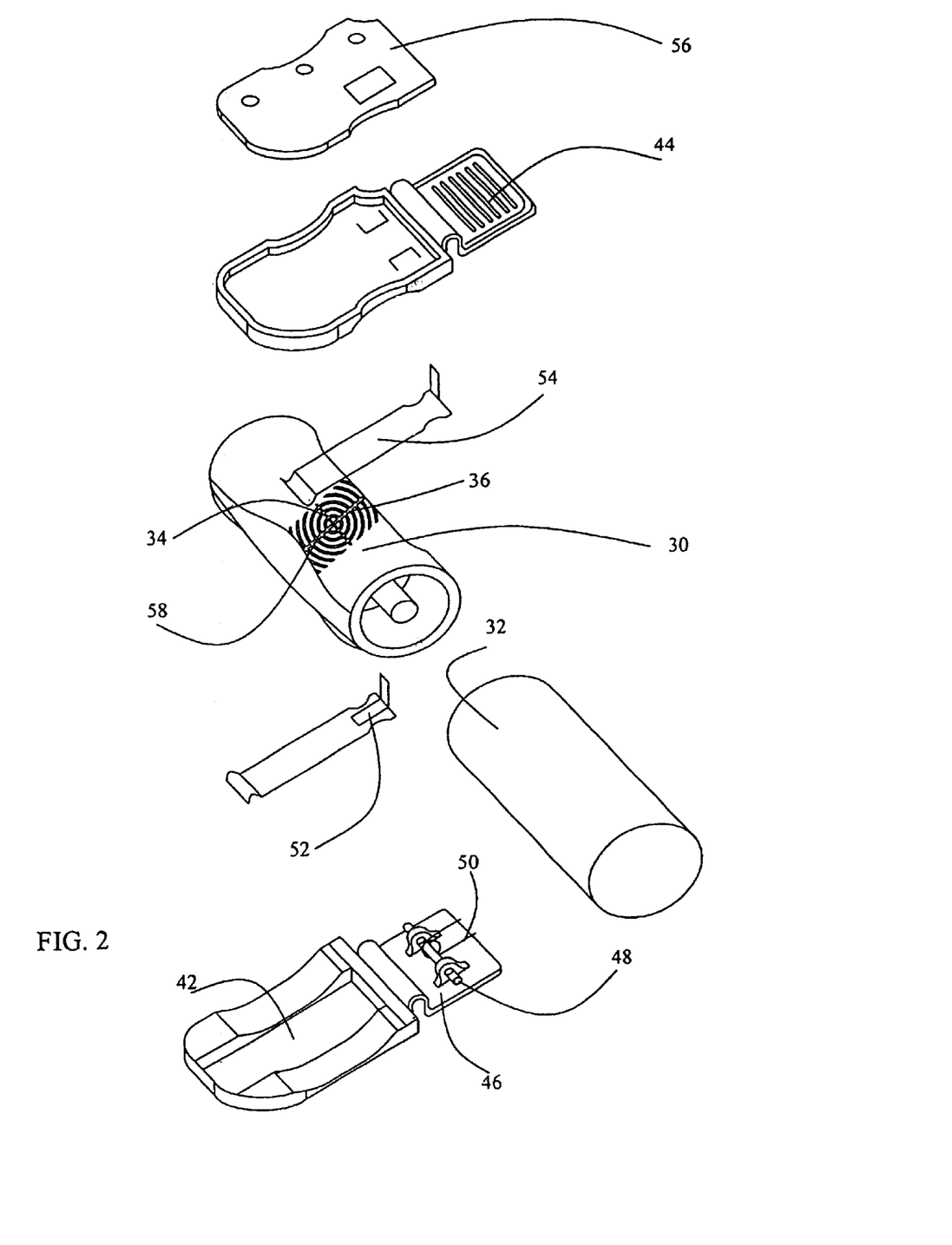
FIG. 2 is an isometric view of the disassembled components of a preferred embodiment of the present invention.

Shown in FIG. 2 are the major components of a preferred embodiment of the present invention. The sheath 32 is fabricated from highly elastic non-permeable material. In use, the sheath is deployed over the housing 30. The length of the periphery of a cross-section taken at any point along the length of the housing will be a substantially constant. That is, even though the shape of the housing changes, the distance around it remains the same over the entire length of the housing. The relationship of the length of the cross-sectional periphery of the housing to the inside diameter of the sheath is such that, when in place, the sheath tightly wraps the housing along its length, leaving the ends uncovered. Pressure-sensing regions 58 are defined by flattened, and transversely elongated, areas located on opposite sides of the housing substantially midway along the length of the housing. In the embodiment shown here, these pressure-sensing regions contain a series of interconnected channels 36 (shown in greater detail in FIG. 4) that substantially encircle the opening of a pressure-release passage 34 in the exterior wall of the housing. These channels facilitate the dispersal of the fluid within the pressure-sensing region, thus creating a larger area over which any changes in fluid pressure acts. As a result, the pressure-sensing region is a hydraulic amplifier that magnifies the small change in fluid pressure from negative to positive so as to be more readily discernable. The pressure-sensing region is the containment volume between the exterior wall of the housing and the sheath that is created by the channels. The pressure-release passages allow fluid to flow from the fluid passageway inside the housing through to the respective pressure-sensing regions. The housing is configured with connection extensions 38 at each end for direct connection with the tubing used in an intravenous delivery system. The housing with the sheath deployed around it will be referred to herein as the "conduit body."

Deployed around the conduit body is a battery powered sensing mechanism. The components illustrated in the embodiment here form a clamp apparatus with electrical contacts 52 and 54 attached to the inside surfaces of the jaws of the clamp. As the tabs 44 and 46 are pressed toward each other, the two clamp housing pieces 40 and 42 rotate about an axle 48 causing the clamp to open like jaws. When opened, the clamp may be easily deployed around the conduit housing. When the tabs are released a spring 50 forces the jaws closed thereby holding the sensing mechanism in place. With the clamp closed the electrical contacts 52 and 54 touch each other thereby closing an electrical circuit. The electrical contacts are electronically coupled to a battery powered indication system housed under cover 56. It should be noted that the indication system may include any of a number of components such as, but not limited to, visual indicators like LCD read-outs, LED's, or small incandescent or neon light bulb, which may flash or vary their intensity, or audible indicators like buzzers or small speakers, which may produce intermittent or substantially constant tones that may vary in volume or frequency.

Figure 6:
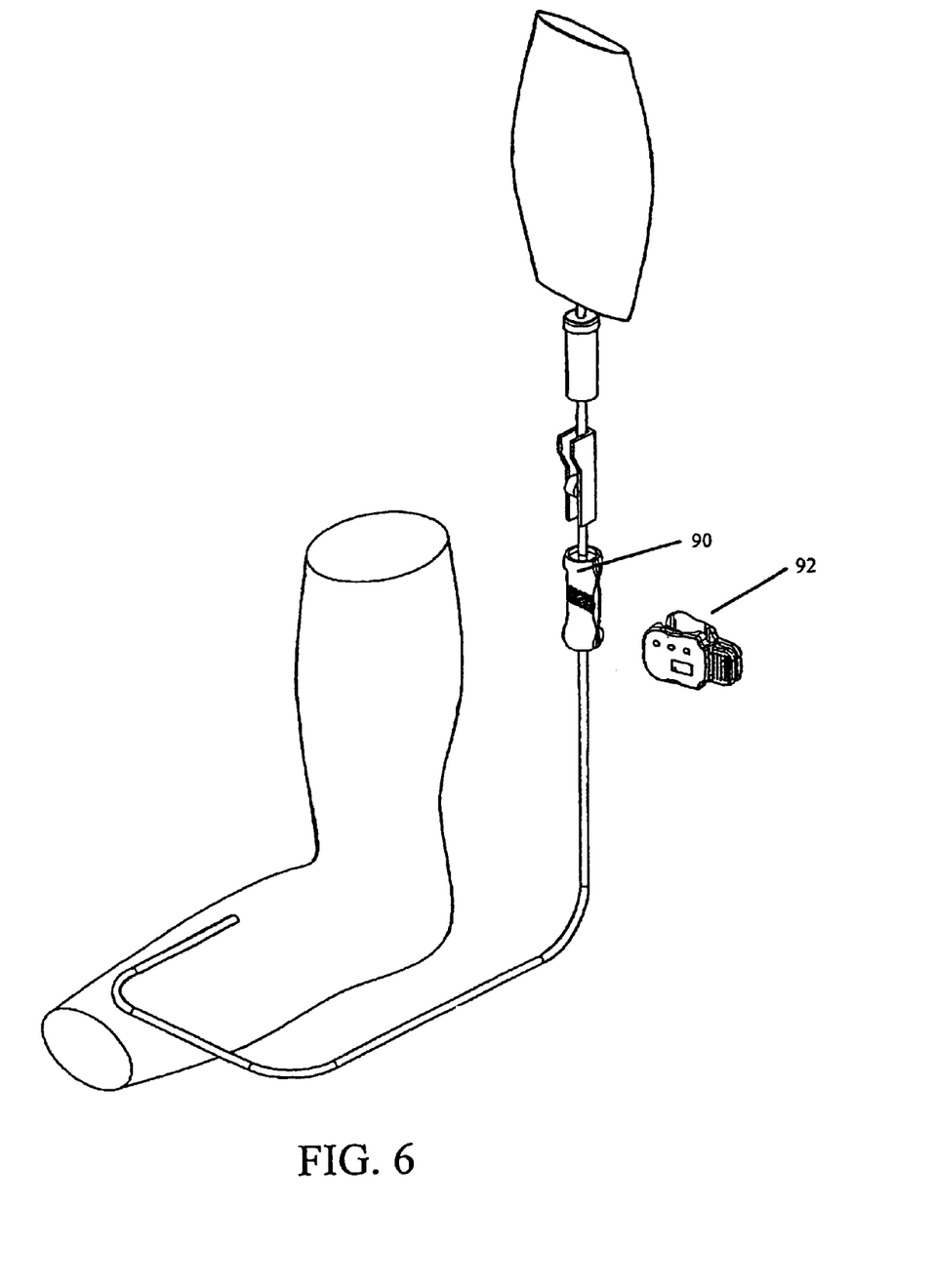
Figure 7:
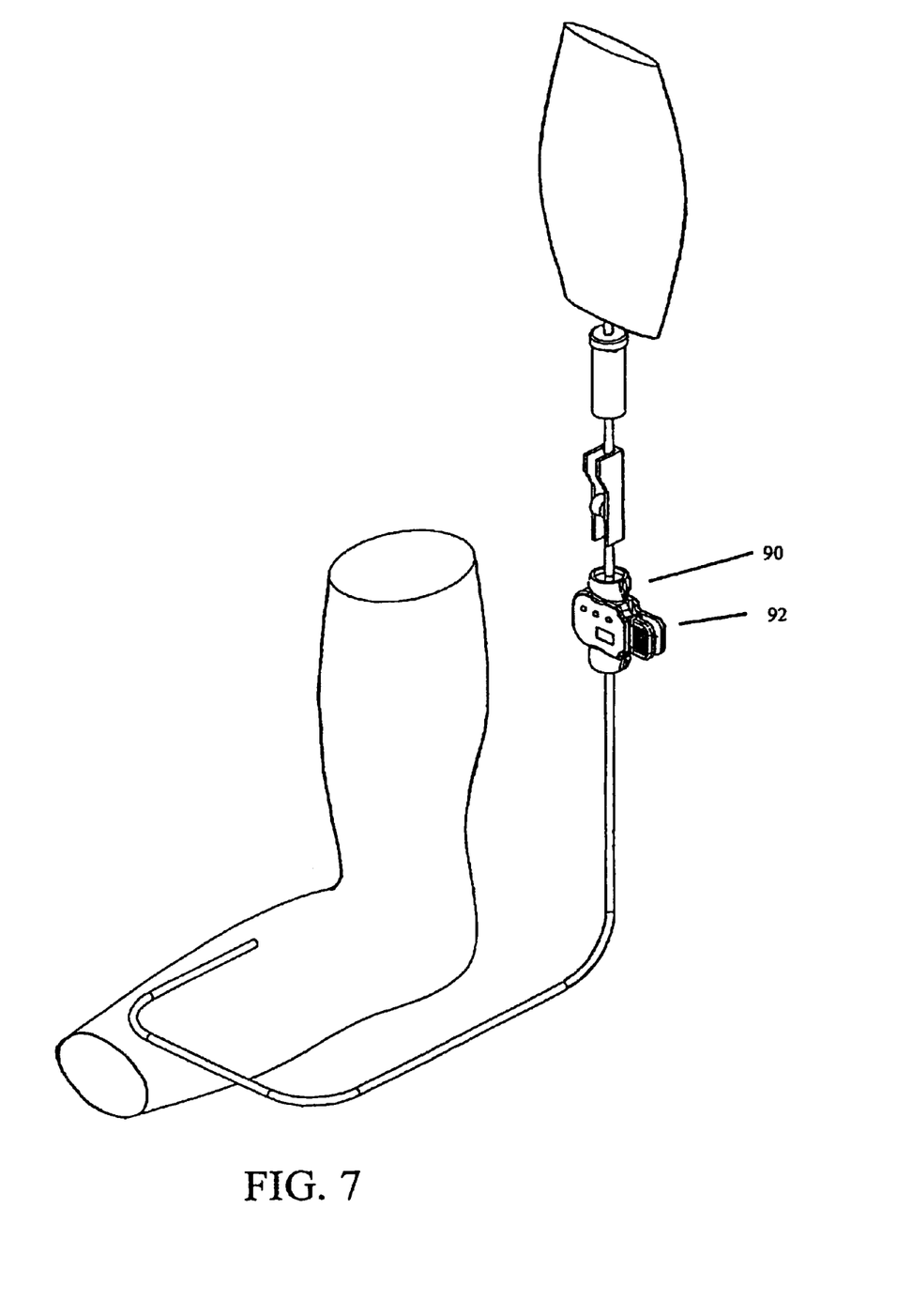

Operation of the device is as follows. The conduit body is adjoined to the intravenous delivery system by interconnection with the tubing below the flow-rate valve, as shown in FIG. 6 Preferably, the placement of the conduit body is as close to the flow-rate valve and as for from the catheter as possible. An alternative means of placement may be by way of a pre-assembled unit including the conduit body and tubing. The sensing mechanism is clamped around the conduit body, as shown in FIG. 7, the catheter is then inserted into the patient and the flow of fluid is begun. As the fluid flows through the conduit body, fluid passes through the pressure-release passages into the pressure-sensing regions. When the flow is normal and unobstructed, the pressure in the conduit body, that is, inside the housing and in the pressure-sensing regions, will be negative and the atmospheric pressure outside will press the sheath against the housing The electrical contacts in the sensing mechanism rest directly on the sheath proximal to the pressure-sensing regions. When the sheath is tight against the housing, the contacts touch, thereby closing an electric circuit. If there is a malfunction that causes an obstruction in the flow of the fluid in the tubing to the catheter, the pressure in the conduit body rises. A common example of this would be the catheter tip being located in body tissue, resulting in extravasation. If the pressure in the conduit body, and therefore in the pressure sensing region, becomes positive, that is, greater than the atmospheric pressure, the area of the sheath proximal to the pressure sensing regions is forced to expand. The expansion of the sheath forces the electrical contacts in the sensing mechanism apart thereby opening the electrical circuit. When the circuit is opened, the indication system indicates a malfunction by emitting, an audible indication, a visual indication or both. The sensing mechanism may utilize sensors such as, but not limited to, electrical contacts that are forced together thereby closing a circuit or micro-switches.

It should be noted that the components of the conduit body of the preferred embodiment shown here are designed for fabrication from inexpensive materials and the entire conduit body is intended for disposal after a single use The sensing mechanism and the indication system, however, are housed in a clamp apparatus that is configured for reuse. Since the electrical components of the embodiment described here are battery powered, the clamp apparatus is self-contained, relatively small and easy to use. The inside surfaces of the jaws of the clamp are contoured to fit the shape of the housing, thereby automatically aligning the electrical contacts with the pressure-sensing regions. This makes the end use for medical personnel simple and the cost of the device for medical institutions very low.

Another feature is that the present invention does not need to be reset, calibrated, nor have current parameters set for each use, as is the case with detectors and alarm systems of prior art This feature is of tremendous value with regard to the initial insertion of the catheter into the patient. With the devices of prior art, the parameters for determining a malfunction are based on flow rates or other criteria established after the catheter is in place. Even if the initial placement of the catheter is inappropriate, the initial flow rate may be calibrated as acceptable. This is not the case with the present invention. No calibration is required. The criterion for detection of malfunction is objective and concise, the change of pressure in the conduit body from negative pressure to positive pressure. The threshold for activation is extremely low in comparison to that of systems of prior art. The present invention not susceptible to false indications even be fore the system is deployed for use in the patient. This renders the present invention able to respond substantially from of the outset of fluid delivery and the response to malfunction is substantially immediate. That is, the device of the present invention may be in place and operative so that if the placement of the catheter in the initial insertion is inappropriate, with the tip in tissue rather than the desired blood vessel, the present invention will emit an indication alerting the medical staff. This ability is unique over the systems of prior art, as is the low cost and ease of operation mentioned above. An alarm will also be emitted in cases where the flow-rate valve malfunctions allowing un-regulation flow, as shown by line 12 in FIG. 1, which is the result of a fully open flow-rate valve and a properly functioning catheter.

Figure 3A:
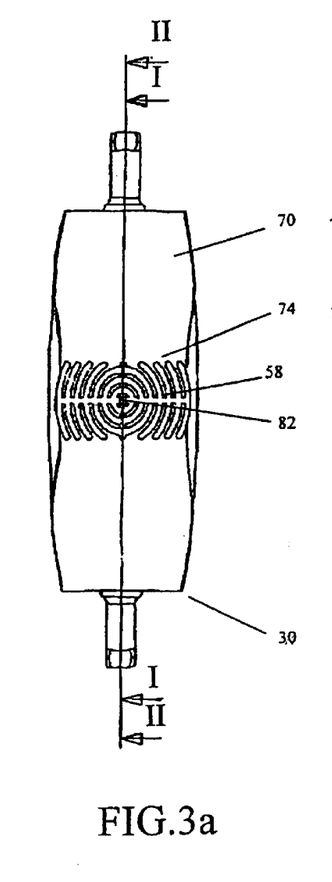
FIG. 3a is a front elevation of a conduit body of a preferred embodiment of the present invention.

FIG. 3a provides a closer look at the front elevation, 3b is a cross-section along line A—A, and 3c is a cross-section alone line B—B of the conduit body of as discussed above in FIG. 2. A cross-section taken at either of the end regions 70 and 72 is substantially circular, to accommodate interconnection with the intravenous delivery system tubing. The middle region 74 is substantially flattened to provide for the pressure-sensing regions 58 and to accommodate the clamp embodiment of the sensing mechanism previously mentioned. As seen here in FIG. 3b, the elasticity of the sheath 32 results in the sheath fitting lightly over the full length of the housing 30. It should be note that various shapes and exterior dimensions of the housing and shapes and elastic properties of the sheath or the use of additional sealing elements may result in providing a sealed pressure-sensing region in the conduit body are with in the scope and intentions of the present invention.

Figure 3B:
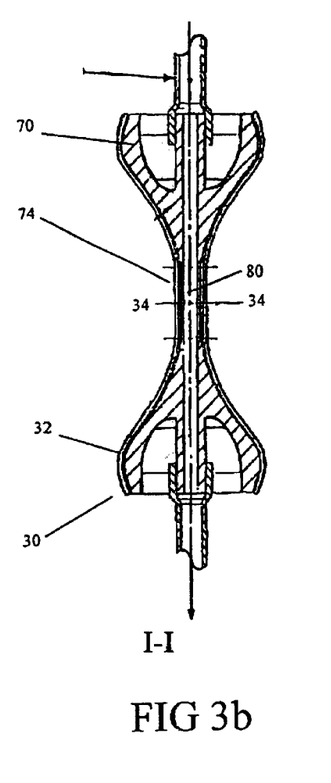
FIG. 3b and FIG. 3c are cross sections along line A—A and B—B respectively.
Figure 3C:
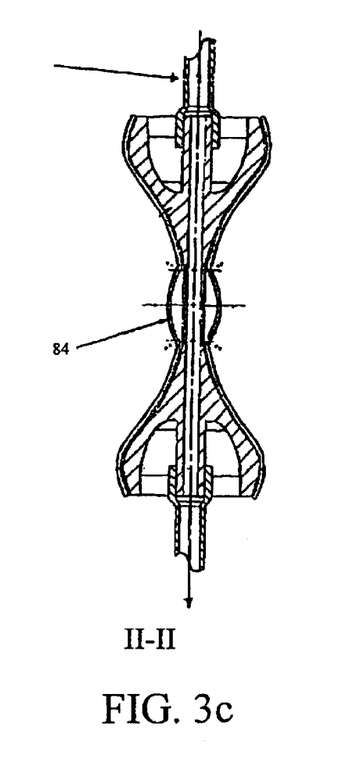

FIGS. 3b and 3c shown, in detail, an implementation of the pressure-release passages 34 connecting the fluid passage 80 to the pressure-sensing regions 58. FIG. 3a shows the sheath while the pressure in the fluid passage is below atmospheric pressure. FIG. 3c shows the expansion of the sheath when the pressure in the fluid passage rises above atmospheric pressure.

Figure 4:
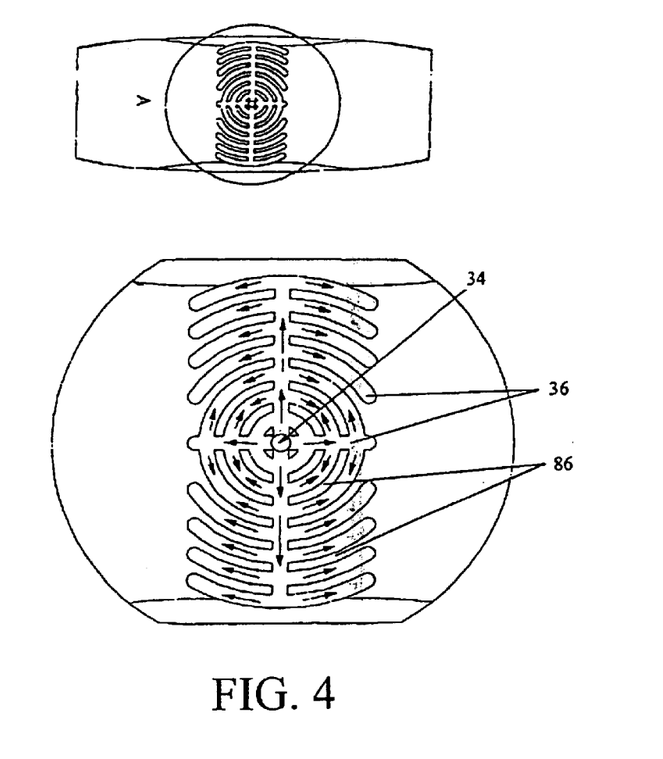
FIG. 4 is a detail of the channels and ridges of the pressure sensing area of FIG. 2.
Figure 5:
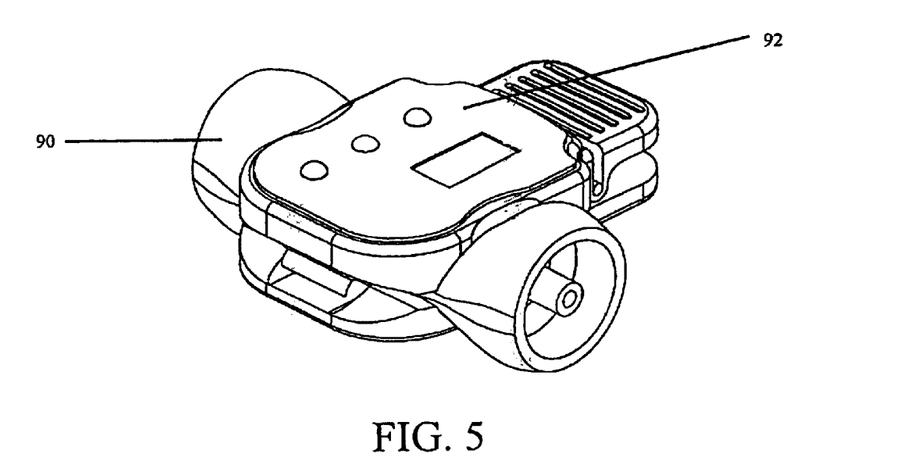
FIG. 5 is an isometric view of a fully assemble preferred embodiment of the present invention.

FIG. 4 gives a detailed look at the pressure-sensing region. The channels 36 that extend into the exterior wall allow the fluid to spread throughout the pressure-sensing region after it passes through the pressure-release passage 34. The channels are separated by ridges 86 that support the sheath above the channels. The arrows show the path of fluid spreading in the pressure-sensing region. It should be noted that the pressure-sensing regions may be formed by ridges which extend above the surface of the housing wall, channels which extend into the housing wall, or any combination thereof.

FIGS. 6 and 7 are identical and are numbered accordingly. Both figures show the components of an intravenous delivery system including a preferred embodiment of the present invention, together with an arm. In FIG. 6 the conduit body 90 is interconnected with the delivery tubing and located directly below the flow-rate valve. The clamp apparatus 92 is position for deployment around the conduit body. FIG. 7, the clamp apparatus 92 is in place around the conduit body 90 and the system is ready for use.

Figure 8:
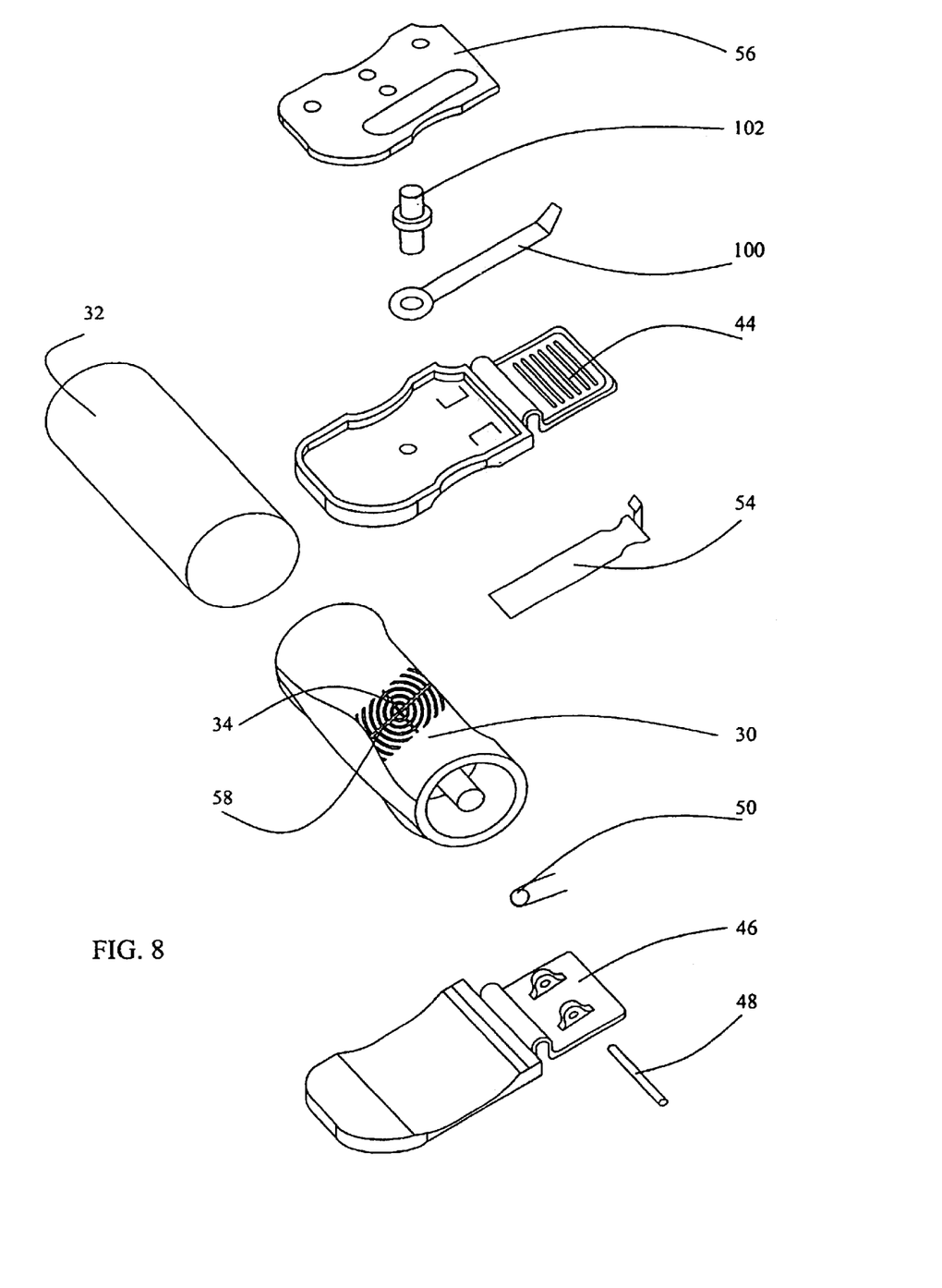
FIG. 8 is an isometric view of the disassembled components of an alternative preferred embodiment of the present invention.

FIG. 8 shows the major components of an alternative preferred embodiment of the present invention that utilizes a sensing unit with electrical contacts that close, that is come together. Many of the parts shown here are identical to, and perform the same function as, those shown in FIG. 2, and are therefore numbered accordingly. Of particular interest here are the electrical contact 100 and the associated adjustment screw 102. As discussed at length above, when the pressure in the fluid passage becomes positive the sheath expands. In the embodiment shown here, there is only one pressure-release passage 34 opening into a single pressure-sensing region 58. The adjusting screw 102 is in constant contact with electrical contact 100, and in close proximity to the electrical contact 54 that is resting directly on the sheath. When the sheath expands, electrical contact 54 moves and touches the adjusting screw thereby completing an electrical circuit, this in turn sets off an alarm. It will obvious to one skilled on the art, that a conduit body with two pressure-release passages and corresponding pressure-sensing regions, as discussed in FIG. 2, would function proficiently with this pressure sensing configuration.

It will be appreciated that the above descriptions are intended only to serve as examples, and that many other embodiments are possible within the spirit and the scope of the present invention.

What is claimed is:

1. A device for detecting malfunction of a gravity fed intravenous delivery system that includes a fluid reservoir, a fluid flow-rate valve, and tubing for delivery of the fluid from the container to a catheter, the catheter being inserted intravenously in a patient, the device comprising:
   (a) a conduit body including:
      (i) a housing configured for interconnection with the tubing, fluid flowing through an interior flow passage in said housing, said housing including at least one pressure release passage to allow the fluid to pass between said interior passage and a pressure-sensing region; and
      (ii) an elastic non-permeable sheath deployed so as to circumscribe said housing such that said pressure-sensing region is located between an exterior wall of said housing and said sheath, wherein said sheath is configured such that, when a fluid pressure within said interior flow passage is less than atmospheric pressure, said sheath is pressed against said housing and, when a fluid pressure within said interior flow passage rises above atmospheric pressure, said sheath expands;
   (b) a sensing mechanism deployed around said conduit body, said sensing mechanism including at least one sensor configured to discern the expansion of said sheath; and
   (c) an indication system coupled to said sensor.

2. The device of claim 1, wherein said housing has a shape such that the length of an outer periphery of a cross-section is substantially constant for any cross-section along the length of said housing.

3. The device of claim 1, wherein a cross-section of said housing taken at a point in either end region will have a substantially circular outer shape to facilitate interconnection with said tubing, and a cross-section taken at a point in a middle region will have a substantially elongated outer shape configured to provide a substantially flat area for said pressure-sensing region.

4. The device of claim 1, wherein said housing further includes a pattern of flow channels located in said pressure-sensing region substantially encircling an open end of said pressure-release passage, said flow channels being configured so as to facilitte diffusion of said fluid within said pressure-sensing region.

5. The device of claim 4, wherein said flow channels are formed between ridges that extend above a surface of said exterior wall.

6. The device of claim 1, wherein said sensor includes electrical contacts deployed around said conduit body.

7. The device of claim 6, wherein said discernment includes a change in status of said electrical contacts.

8. The device of claim 7, wherein said change in status includes the separation of said electrical contacts thereby opening an electrical circuit, said separation being caused by said expansion of said sheath.

9. The device of claim 1, wherein said sensing mechanism and indication system are housed in a clamp apparatus configured for repeated deployment, said deployment being around said conduit body.

10. The device of claim 1, wherein an audible indication is emitted by said indication system.

11. The device of claim 1, wherein a visual indication is emitted by said indication system.

12. The device of claim 1, wherein said sensing mechanism is battery powered.

13. The device of claim 1, wherein said indication system is battery powered.

14. A method for detecting malfunction of a gravity fed intravenous delivery system that includes a fluid reservoir, a fluid flow-rate valve, and tubing for delivery of the fluid from the container to a catheter, the catheter being inserted intravenously in a patient, the method comprising:
   (a) monitoring a direction of pressure difference between ambient atmospheric pressure and the fluid inside the tubing, said direction of pressure difference being monitored at a location chosen such that, during normal operation of the gravity fed intravenous delivery system, the pressure of the fluid is normally below atmospheric pressure; and
   (b) activating an alarm when said pressure inside the tubing exceeds atmospheric pressure.

15. The method of claim 14, wherein said monitoring is accomplished by:
   (a) interconnecting a conduit body with the tubing, said conduit body including:
      (i) a housing configured for interconnection with the tubing, fluid flowing through an interior flow passage in said housing, said housing including at least one pressure release passage to allow the fluid to pass between said interior passage and a pressure-sensing region; and
      (ii) an elastic non-permeable sheath deployed so as to circumscribe said housing such that said pressure-sensing region is located between an exterior wall of said housing and said sheath;
   (b) deploying a sensing mechanism around said conduit body, said sensing mechanism including at least one sensor configured to discern the expansion of said sheath, said expansion being caused by an increase of said fluid in said pressure sensing region due to increased fluid pressure in the tubing and said housing, said sensing mechanism being further connected to an indication system.

16. The method of claim 15, wherein said discerning includes changing status of electrical contacts that are deployed around said conduit body, said electrical contacts being included in said sensing mechanism.

17. The device of claim 16, wherein said changing status includes separating said electrical contacts thereby opening an electrical circuit, said separation being caused by said expansion of said sheath.

18. The method of claim 17, wherein said separation of said electrical contacts activates said indication system.

19. The method of claim 18, wherein said activation of said alarm causes the emittance of an audible indication.

20. The method of claim 18, wherein said activation of said alarm causes the emittance of a visual indication.

21. A system for the intravenous delivery of a fluid into a patient, the system comprising:
(a) the device of claim 1;
(b) tubing interconnected with a fluid flow-rate valve and said conduit body, so as to be a single unit;
(c) a fluid reservoir, configured for interconnection with a top termination of said tubing such that the path of fluid flow passes from said reservoir, through said flow-rate valve, said conduit body, and a remainder of said tubing;
(d) a catheter configured for interconnection with a bottom termination of said tubing; and
(e) a clamp apparatus housing said sensing mechanism and said indication system, said clamp apparatus configured for deployment around said conduit body.

* * * * *